United States Patent [19]
Wurtman et al.

[11] Patent Number: 5,612,320
[45] Date of Patent: Mar. 18, 1997

[54] THERAPEUTIC CARBOHYDRATE BLENDS FOR TREATING AND AIDING PREMENSTRUAL SYNDROME

[75] Inventors: Judith J. Wurtman, Boston, Mass.; Jeff L. Shear; Alvin Kershman, both of St. Louis, Mo.

[73] Assignee: Internutria, Inc., Framingham, Mass.

[21] Appl. No.: 359,695

[22] Filed: Dec. 20, 1994

Related U.S. Application Data

[63] Continuation-in-part of Ser. No. 168,492, Dec. 22, 1993, abandoned.

[51] Int. Cl.$^6$ ..................................................... A61K 31/70
[52] U.S. Cl. ........................ 514/54; 514/58; 514/59; 514/60; 514/899
[58] Field of Search .............................. 514/60, 58, 899, 514/59, 54

[56] References Cited

U.S. PATENT DOCUMENTS

| | | | |
|---|---|---|---|
| 3,867,523 | 2/1975 | Bahal . | |
| 3,892,871 | 7/1975 | Cooper | 426/573 |
| 4,089,944 | 5/1978 | Thomas . | |
| 4,182,860 | 1/1980 | Naslund et al. . | |
| 4,344,968 | 8/1982 | Aoda et al. . | |
| 4,590,075 | 5/1986 | Wei et al. . | |
| 4,591,559 | 5/1986 | Liu et al. . | |
| 4,687,763 | 8/1987 | Wurtman . | |
| 4,753,805 | 6/1988 | Cherukuri et al. | 426/5 |
| 4,971,998 | 11/1990 | Wurtman et al. | 514/654 |
| 5,011,688 | 4/1991 | Calam et al. | 424/195.1 |
| 5,140,021 | 8/1992 | Maxson et al. | 514/177 |
| 5,223,540 | 6/1993 | Wurtman et al. . | |
| 5,266,333 | 11/1993 | Cady et al. . | |

OTHER PUBLICATIONS

Zämblera et al., Treatment of mild premenstrual syndrome. *Contemporary Review of Obstetrics and Gynaecology.* 1993 5:214–220.
International Search Report, dated Mar. 20, 1995.
Fernstrom, J., et al., *Science*, (1971), 178:414–416.
Mortola, J., et al., *Obstet. Gynecol.*, (1990) 76:302–307.
Endicott, J., et al., *Psychopharmacol. Bull.*, (1982) 18(3):121–123.
Shader, R. I., et al., *Psychopharmacol. Bull.*, (1982) 18(3):113–121.
Gronwall, D., et al., *J. of Neurology, Neurosurgery and Psychiatry*, (1981) 44:889–895.
Keenan, P., et al., *Psychoneuro-endocrinology*, (1992) 17:179–187.
Brugger, P. et al., *Percept Mot Skills*, (1993), 77:915–921.
Menkes, D., et al., *J. of Affective Disorders*, (1994) 20:1–7
Boyer, W., *Clin. Pyschopharmacology*, (1992) 6:5–12.
Lieberman, et al., *Am. J. Clin. Nutr.*, (1986) 44:772–8.
O'Rourke, D. J. *Clin. Psychriatry*, (1989) 50:343–347.
Rosenthal, N., et al., *Biol. Psychiatry*, (1989) 25:1029–1040.
Reid, R., *Curr. Probl. Obstet. Gynecol. Fertil.* (1985) 8:1–5.
Lyons, P. M., et al., *Am. J. Clin. Nutr.*, (1988) 47:433–39.
Boyd, N. F., et al., *The Lancet*, (1988), pp. 128–132.

Moller, S. E., *Pharmacol. Toxicol.* 71, Suppl. 1 (1992) 61–71.
Hartmann, M. K., et al., *Sleep* 1978, Fourth European Congress on Sleep Research, TirguMures, (1978), pp. 385–390.
Porter, J. M., et al., *Sleep* 1980, Fifth European Congress on Sleep Research, Amsterdam, (1980), pp. 408–410.
Wurtman, J. J., *Clinical Neuropharmacology*, (1988), vol. 11, Suppl. 1, pp. S139–S145.
Wurtman, J. J., *Appetite*, (1987) 8:211–213.
Wurtman, R. J., et al., *Appetite*, (1986) 7:99–103.
Wurtman, J. J., *Annals N.Y. Acad. of Sci.*, (1985), 443–145–51.
Wurtman, J. J., *J. of the American Dietetic Assoc.*, (1984) 84(9):1004–1007.
Spring, B., et al., *J. Psychiat. Res.*, (1982) 17(2):155–67.
Heraief, E., et al., *J. Neural Transmission*, (1983) 57:187–195.
Wurtman, J. J., et al., *Neuropsychopharmacology*, (1993), vol. 9, No. 3, pp. 201–210.
Wurtman, R. J., et al., *The Biology of Feast and Famine*, Academic Press, pp. 151–156.
Wurtman, J. J., et al., *Current Med. Res. and Opinion*, vol. 6, Suppl. 1, (1979), pp. 28–33.
Wurtman, J. J., *Drugs*, (1990) 39(3):49–52.
Spellacy, W. N., et al., *J. Reproductive Medicine*, (1990), pp. 508–511.
Spring, B., et al., *Nutr. Health*, (1984), 3:(1–2)55–67.
Porter, J. M., et al., *Electroencephalography & Clin. Neurophysiology*, (1981) 51:426–433.
Neumann, M., et al., *Perceptual and Motor Skills*, (1992) 75:873–874.
Francart, A.-L., et al., *C.R. Soc. Biol.*, (1989) 183:467–473.
Hurni, M., et al., *Br. J. Nutr.*, (1982) 47(1):33–44.
Pollet, P., et al., *Int. J. Vitam. Nutr. Res.*, (1983) p. 223.
Hartmann, M. K., et al., *Waking and Sleeping*, (1979) 3:63–68.
BOOK:Smith, S., et al., *Modern Management of Premenstrual Syndrome*, Norton Medical Books, W.W. Norton & Co. (1993) (copy not included in references).
McNair, et al., *Profile of Mood States Manual (POMS)* (1971–1981), San Diego Educational and Industrial Testing Service.
Wurtman, J. J., *J. Clin. Psychiatry*, (1988) 49(8):37–39.
Smith, S. L. et al., *Psychosomatic Medicine*, (1969) 31:281–287.

(List continued on next page.)

*Primary Examiner*—James O. Wilson
*Attorney, Agent, or Firm*—Lowe, Price, LeBlanc & Becker

[57] ABSTRACT

A composition is disclosed for alleviating or managing symptoms associated with premenstrual syndrome "PMS" comprising an effective amount of an aqueous mixture of water and a rapidly digestible carbohydrate blend. The aqueous mixture is essentially free of protein and is characterized by a certain pH and ratio of water to carbohydrate blend. Methods of use of the composition for alleviating or managing symptoms associated with PMS are also disclosed.

41 Claims, No Drawings

OTHER PUBLICATIONS

Abraham, G. E., et al., *J. Reprod. Med.*, (1987) 32:405–422.

Wurtman, J. J., et al., *Am. J. Obstet. Gynecol.*, (1989) 161:1228–1234.

Sayegh, R., et al., *J. Am. Med. Assoc.*, "The Effect of a Carbohydrate–Rich Beverage on Mood, Appetite and Cognitive Function in Women with Premenstrual Syndrome," (1995).

Abraham, G., *Current Progress in Obstet. and Gynecol.*, (1980), 3:5–39.

Steiner, M., *Clin. Obstet. Gynecol.*, (1992) 35:599–611.

Wood, S. H., et al., *Obstet. Gynecol.*, (1992) 80:339–44.

Bancroft, J., et al., *Psycho. Med.*, (1988) 18:855–860.

Brzezinski, A. et al., *Obstet. Gynecol.*, (1990) 76:206–301.

Elia, D., et al., *Revue Francaise de Gynecologie ed d'Obsterique*, (1992) 87:361–369.

Elks, M., *Southern Med. J.*, (1993) 86:503–507.

Stone, A. B., et al. *Psychopharmacol. Bull.*, (1990) 26:331–335.

Stone, A. B., et al., *J. Clin. Psychiatry*, (1991) 52:290–293.

Bancroft, J., et al., *Psychosomatic Medicine*, (1993) 55:133–145.

THERAPEUTIC CARBOHYDRATE BLENDS FOR TREATING AND AIDING PREMENSTRUAL SYNDROME

CROSS-REFERENCES TO RELATED APPLICATIONS

The instant Ser. No. 08/359,695 is a continuation in part of U.S. patent application Ser. No. 08/168,492 filed Dec. 22, 1993, now abandoned the entire disclosure of which is incorporated by reference herein.

FIELD OF THE INVENTION

The present invention relates generally to novel therapeutic compositions comprising carbohydrate blends and to methods of using the foregoing for the treatment of premenstrual syndrome (PMS).

BACKGROUND OF THE INVENTION

Each month, for a few days prior to the onset of menstruation, many millions of otherwise-healthy American women develop symptoms of disturbed mood and appetite that can be strikingly similar to those reported by patients with Seasonal Affective Disorder (SAD), carbohydrate-craving obesity, or the non-anorexia variants of bulimia. This syndrome was first termed "premenstrual tension" by R. T. Frank in 1931 and is a very common phenomenon. According to Guy Abraham of UCLA, " . . . of every ten patients to walk into a gynecologist's office, three or four will suffer from premenstrual tension . . . ", and in some the symptoms will be of such severity as to include attempts at suicide. *Current Progress in Obstetrics and Gynecology*, 3:5–39 (1980).

Initial descriptions of the Premenstrual Syndrome (PMS) focused on its association with "nervous tension", headache and weight gain The weight gain observed initially was attributed to excessive retention of salt and water, which does indeed occur in some PMS patients. However, it soon became evident that it was also a consequence of the widespread tendency of PMS individuals to crave and over-consume carbohydrates, particularly foods with a sweet taste. PMS is also now referred to as late luteal phase syndrome. D.N.S. III, Revised, American Psychiatric Association (1987).

There have been numerous suggestions made about the etiology of PMS. For example, some hypothesized that it was caused by a uterine toxin. Others suggested its cause to be over-consumption of sweets, which presumably is followed by excessive insulin secretion, hypoglycemia, and inadequate brain glucose and results in the oft observed depression and anxiety. It also has been postulated that the behavioral symptoms result from tissue edema and that the psychological changes result from feelings of loss or the social complexities generated by the discomforts of menstruation.

However, none of these theories has been substantiated. PMS can persist after hysterectomy and, hence, uterine toxins cannot be its cause. The hyperinsulinism of PMS is not associated with low blood glucose levels, and is probably the consequence of a behavioral aberration (i.e., the tendency of premenstrual women to choose high-carbohydrate diets, which potentiate insulin secretion) rather than the cause. The mood and appetitive changes of PMS are poorly correlated with the tissue swelling; and subhuman primates who are presumably exempt from the psychodynamic or social complexities of human life, also exhibit characteristic behavioral changes premenstrually.

There have been many treatments suggested for overcoming or reducing the symptoms of PMS. Many of these are pharmaceuticals such as vitamin supplements, ovarian hormones, detoxifying agents, and diuretics. Other, non-pharmaceutical treatments include carbohydrate-free diets and irradiation of the ovaries and pituitary. These approaches all have had limited success, however. Currently there is no means of treating the mood and appetite disturbances commonly experienced on a recurring basis by a large number of women. Such a treatment would be of great benefit. The present invention is directed to addressing these, as well as other, important needs.

Serotonin disturbance and/or deficiency is emerging as a leading theory behind the symptoms of PMS. A number of studies have shown that women with PMS have lower serotonin levels than women without PMS.

In mammals, the amino acid tryptophan is the precursor to serotonin synthesis in the brain. Certain carbohydrates when ingested can increase the ratio of tryptophan to large neutral amino acids (T:LNAA) in the blood stream. This increase of T:LNAA allows a higher level of tryptophan to enter the brain, which is necessary for increasing serotonin synthesis. While carbohydrates from normal food can shift this T:LNAA ratio to a limited extent, these normal foods also contain fats and other fibers, both of which slow down digestion and otherwise interfere with the necessary shift in the balance of amino acids in the blood. This invention provides novel carbohydrate blends comprising simple carbohydrates that are rapidly digested and thereby provide relief from the symptoms of PMS, much faster than relief from "normal food".

SUMMARY OF THE INVENTION

The present invention is directed generally to novel therapeutic compositions comprising rapidly-digestible carbohydrate blends, and to methods of using same for the treatment, prevention, amelioration, or dietary management of PMS. Administration of a composition according to the method of the present invention is of great benefit to women who experience disturbances of mood and/or appetite prior to onset of their menstrual period, as the composition, by supplying particular nutrients for the dietary management of PMS, acts to alleviate and/or prevent such adverse premenstrual symptoms.

Specifically, in one embodiment, the present invention is directed to therapeutic compositions useful for the treatment, prevention or dietary management of PMS, comprising novel blends of carbohydrates, such as, but not limited to, dextrose, galactose, pre-gelatinized starch, mannose, sucrose, maltose, lactose, dextrin, maltodextrin, mixtures thereof, and which are essentially free of and not more than 1–2 grams of fat. Preferably, said therapeutic compositions include carbohydrate blends comprising about 20–100 g of a rapidly-digestible carbohydrate blend in solution essentially free of protein, wherein the solution comprises a ratio of about 3–12 mL water to about total 1 g carbohydrate blend and an acidulant selected from the group consisting of adipic acid, citric acid, fumaric acid, lactic acid, succinic acid, tartaric acid, ascorbic acid, acetic acid, and malic acid, to maintain a therapeutically effective pH at less than 6 and wherein the carbohydrate blend comprises about 60–100% dextrose, dextrin, maltodextrin, or a mixture thereof, and 0 to 40% starch or pre-gelatinized starch, or a mixture thereof.

More preferable said carbohydrate blends comprise novel mixtures of dextrose and starch, particularly in ratios of about 80% to 100% dextrose to 0 to 20% starch, wherein the total amount of carbohydrate in said blend comprises about 40–80 grams. Still more preferred are compositions comprising carbohydrate blends of dextrose and starch in ratios of about 80% to 85% dextrose to 15 to 20% starch. Specifically preferred is a composition comprising a carbohydrate blend of 45 g dextrose and 3 g starch.

In another embodiment, said carbohydrate blends are in the form of a solution comprising dextrose, starch and water. Preferably, the solution comprises about 2–10 mL of water to 1 gram of carbohydrate blend. More preferably, the solution comprises about 5–6 mL water to 1 gram of carbohydrate blend.

A further embodiment of the invention is directed to compositions wherein the solution further comprises an acidulant to maintain a therapeutically effective pH at less than 6. Such acidulants include, but are not limited to, adipic acid, citric acid, fumaric acid, lactic acid, succinic acid, tartaric acid, ascorbic acid, acetic acid, and malic acid. Preferred are solutions with a pH between about 2 and 5. More preferred is a solution comprising 60 g dextrose and 10 g galactose, 280 mL water and malic acid to maintain the solution at a pH of 2.

Another embodiment of the invention is directed to methods of using said therapeutic compositions for treating, preventing, ameliorating, or managing the effects of PMS. Such methods comprise administering a therapeutically effective amount of said novel compositions to subjects in need of such treatment. Without limiting the invention, and by way of theoretical hypothesis only, it is believed that such therapeutic compositions are effective by increasing the ratio of T:LNAA in the blood stream thereby increasing the level of serotonin production in the brain. Such increase is believed to relieve those PMS conditions related to serotonin and brain functioning by supplying the nutrients necessary for serotonin synthesis.

A further embodiment of the invention is the method of treating, ameliorating, preventing or managing the symptoms of PMS comprising administering a combination of novel carbohydrate blend compositions of the present invention together with other useful agents, such as but not limited to vitamins; tryptophan, tyrosine, and other amino acids; ovarian hormones; detoxifying agents and/or diuretics.

It is also conceivable that novel compositions of present invention could potentially be useful for the treatment of other symptoms and disorders such as appetite control including carbohydrate craving and binge eating; anxiety and depression and smoking disorders in a subject.

DETAILED DESCRIPTION OF THE INVENTION

The invention describes novel, rapidly-digestible, carbohydrate blend compositions effective to relieve, treat, ameliorate or manage, the symptoms of PMS. The compositions of the present invention comprise 40 to 100% dextrose and 0 to 60% starch, or any other carbohydrate in the carbohydrate blend solution. The more preferred blend is about 80% dextrose and 20% starch. The choice of a particular ratio will depend upon several factors such as the weight of the individual, the rate of effect the carbohydrates have on the subject and the nature and severity of the PMS symptoms or the manner in which the carbohydrate blend is used.

The phrases "carbohydrate blend" or "blend", as used herein and in the claims, refer to mixtures of simple or complex, rapidly-digestible carbohydrates such as, but not limited to, dextrose, galactose, pre-gelatinized starch, mannose, sucrose, maltose, lactose, dextrin, maltodextrin. In a preferred embodiment of the invention, the carbohydrate blend comprises dextrose and starch. The term "dextrose" as used herein and in the claims refers to glucose or polymers thereof.

Carbohydrates of the present invention can be obtained from a variety of commercial sources. However, lactose is comprised of 50% dextrose and 50% galactose and galactose is currently only available when lactose is digested. Galactose may be obtained by a process comprising the steps of hydrolysing lactose, crystallizing the products, drying the products and adjusting the ratio of dextrose to galactose by adding anhydrous dextrose. More preferred is the process wherein the hydrolysing step comprises acid or lactase enzymatic hydrolysis. Also more preferred is the process wherein the crystallization step comprises selectively and separately crystallizing the products dextrose and galactose or crystallizing both dextrose and galactose together.

The term "solution" as used herein and in the claims, refers to mixtures of carbohydrate blends in water. The term "water", as used herein and in the claims, includes distilled, deionized, or tap water. Preferred is a solution further comprising an acidulant, to maintain a therapeutically effective pH below about 6. The term "acidulant", as used herein, includes acids which can maintain a therapeutically effective pH of the solution. Such acids include but are not limited to adipic acid, citric acid, fumaric acid, lactic acid, succinic acid, tartaric acid, ascorbic acid, acetic acid, and malic acid. Preferred is the acidulant malic acid. The phrase "therapeutically effective" as used herein and in the claims refers to that amount of carbohydrate blend necessary to administer to a subject to induce the desired effect of treating, ameliorating, relieving, or managing the symptoms of PMS.

Yet another embodiment of the invention is directed to a method of treating PMS comprising the administration such novel compositions. Such method comprises administering said therapeutic composition to an individual, prior to the onset of her menstrual period, in a quantity sufficient to reduce, ameliorate, manage or prevent the mood and/or appetite disturbances, and/or to suppress the weight gain, which otherwise would be observed in the individual prior to onset of menstruation. One or more of the compositions of this invention can be administered for the treatment of PMS by any means that produces contact of the active agent with the agent's site of action in the body of a mammal. Preferably, the compositions are administered orally. They can be administered by any conventional means available for use in conjunction with therapeutic or dietary agents. They can be administered alone, but generally administered with a carrier selected on the basis of the chosen route of administration and standard therapeutic practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 20–100 g, with the preferred dose being about 40–60 g.

The length of time during which a therapeutic compositions will be given varies on an individual basis, but will generally begin 1 to 14 days prior to menstruation and may continue for several days (e.g., 3 days) after onset of menstruation.

Dosage forms (compositions suitable for administration contain) from about 20–100 g of active ingredient per unit. In these therapeutic compositions the active ingredient will ordinarily be present in an amount of about 0.5–95% by weight based on the total weight of the composition.

The active ingredient can be administered orally in solid dosage forms, such as capsules, tablets, and powders when taken with a suitable amount of water, or in liquid dosage forms, such as elixirs, syrups, and suspensions so long as the proper ratios of ingredients are maintained. Gelatin capsules contain the active ingredient and other powdered carriers, such as cellulose derivatives, magnesium stearate, stearic acid, and the like. Similar diluents can be used to make compressed tablets. Both tablets and capsules can be manufactured as sustained release products to provide for continuous release of agent over a period of hours. Compressed tablets can be sugar coated or film coated to mask any unpleasant taste and protect the tablet from the atmosphere, or enteric coated for selective disintegration in the gastrointestinal tract.

Further, the therapeutic compositions can also be prepared in the form of a food-stuff. Such forms include but are not limited to: a cold or hot beverage, soup, pudding, wafer, candy, a snack bar, or other snack, etc.

Various colorings and flavorings can be employed in any of the above-mentioned dosage forms to improve the taste of the therapeutic composition to increase patient acceptance, and to make it more palatable. Such flavorings can include but are not limited to artificial or real: chocolate, vanilla, strawberry, coffee, banana, orange, etc.

In these various forms, the compositions can be combined with additional substances, such as those needed to serve as fillers, diluents, binders, flavorings or coloring agents or coating materials.

EXAMPLE 1

"Composition A": 44.5 g of dextrose, 3 g starch, 1.4 g malic acid, pH 2, 270 mL water, orange flavoring.

EXAMPLE 2

60 g dextrose, pH 5, 180 mL water.

EXAMPLE 3

60 g dextrose, pH 2, 360 mL water.

EXAMPLE 4

30 g dextrose, pH 2, 360 mL water.

EXAMPLE 5

HUMAN EFFICACY TEST

Carbohydrate blends of present invention or a placebo solution were tested in subjects with PMS over four menstrual cycles. This study was a randomized, iso-caloric placebo-controlled, double-blind study using a Latin Square cross-over design. The study also incorporated a "matched-samples" group design in which the different testing groups had a similar average magnitude and variance with respect to PMS severity. In order to minimize placebo and first time expectation effects; reduce variability; and increase the power of the experimental design, the study utilized a "Latin Square cross-over" group design after placebo run-in, where the subjects received the iso-caloric placebo during the first test month, and then assigned to one of the treatment arms during the second month, and were finally crossed-over during the third and fourth months. A detailed explanation of the methods, measures, and procedures used to accomplish this follows.

At various times before and after therapy, subjects completed a standard questionnaire entitled Profile of Mood States (POMS) as described in McNair et al., *Profile of Mood States Manual* (1971/1981), San Diego: Educational and Industrial Testing Service, which is incorporated herein by reference in its entirety. The POMS test is a well accepted adjective rating test which was designed to measure multiple dimensions of affect.

Six groups of women with PMS were tested over four menstrual cycles. The subjects were women who were diagnosed with premenstrual syndrome through an Admissions Form, a Health History Form, a Menstrual Symptomatology Questionnaire, a PMS Profile form, and a PMS Symptomatology Calendar (or Daily Diary) recorded on a daily basis. Subjects were considered to be suffering from PMS by consistent worsening of her appetite, mood and impairment ratings during the luteal phase of her cycles. All subjects received placebo during the first test month and then were placed into one of six treatment arms during the second month and finally crossed over during the third and fourth months. During the final 3 months, they received in a double-bind methodology, either a placebo or a carbohydrate blend of the present invention. Subjects in each group were matched according to their follicular and luteal menstrual distress scores obtained in the first month. This ensured that subjects experiencing relatively similar premenstrual distress were placed in each treatment arm.

During the follicular phase, subjects filled out a diary each day and mailed the week's completed form to the study office; during the luteal phase they phoned in their scores each evening. This allowed the study personnel to monitor more closely daily variability and consistency in luteal phase scores. Subjects were tested away from the study site, either in their workplace or at home. They, however, had frequent personal and telephone contact with study personnel prior to and during the testing process.

Acute and chronic effects of each test article were measured using a 29-question PMS Symptomatology Calendar, the Day-4 Acute Appetite, Mood and Cognition tests, and an End-of-Month Questionnaire in which each subject recorded their own subjective observations of the therapy's efficacy. Specific descriptions of the acute measures is given in Table 1.

TABLE 1

| ACUTE MEASURES | |
|---|---|
| Symptom | Measure |
| Appetite | Appetite Questionnaire. A 4-question test using a 10-point scale |
| Mood | Modified Profile of Mood States (POMS). A 26-question test using a 5-point rating scale |
| | Modified Visual Analog Mood Scale (VAMS). A 12-question test using a 10-point scale |
| | Misery Index. An overall emotional functioning rating on a 10-point scale scored as relative to the subjects' worst PMS experience |
| | These are tests rating memory, as well as analytical and verbal capability, and may be sensitive to menstrual cycle. |

TABLE 1-continued
ACUTE MEASURES

| Symptom | Measure |
|---|---|
| Cognition | Paced Auditory Serial Addition Test.<br>Recurrent Consonant Trigrams.<br>Controlled Oral Work Association. |

Specific descriptions of the chronic measures are given in Table 2.

TABLE 2
CHRONIC MEASURES

| Measure | Description |
|---|---|
| PMS Symptomatology Calendar (Daily Diary) | The PMS Symptomatology Calendar was completed in writing during the follicular phase of each subject's cycle and completed over the telephone during each subject's luteal phase (the telephone was used during the more critical luteal phase to ensure that subjects did not wait until a later day to fill out their calendars). The calendar utilized a 6-point scale that consisted of the following:<br>Appetite.        4 questions<br>Mood.            15 questions<br>Impairment.      3 questions<br>Physical.        4 questions<br>Exclusion criteria. 3 questions concerning illness, medication, or stress<br>The mood questions included sleepiness as a symptom that will allow monitoring of that symptom on a chronic basis. |
| Day-4 Acute Testing | Acute tests were taken on both the first and fourth day each month that the subject received therapy. A comparison was made between the subject's scores on the first and fourth days to assess chronic effect of the intervention. |
| End of Month Questionnaire | A 6-question, self assessment was made by each subject as to how well the therapy worked each month in relieving her PMS symptoms (i.e., overall, appetite, mood, cognition, impairment, and physical symptoms). |

Procedures

Subjects entered the study on the day following the onset of menses. They were then monitored and administered the compositions through four menstrual cycles. During all days after the onset of menses and prior to ovulation, the follicular phase schedule was followed and during all days post ovulation and prior to menses, the luteal phase schedule was followed. Determination of the luteal phase of the cycle was done using an ovulation kit. Approximately seven days after ovulation, the subject entered the late luteal phase of the cycle. The specific procedure for these phases are as follows:

Follicular phase schedule.

The schedule outline in Table 3 was followed by subjects during the follicular phase of their cycle, during the first two months only, to establish appropriate baselines for the subjects. The appetite, mood, and cognitive tests was administered at 5:30 PM, because these corresponded to the times that tests were taken during the luteal phase, and represented the time that composition efficacy was expected to be greatest, (i.e. 1.5 hours after composition was consumed at 4:00 PM).

Subjects came to the study office prior to the first at-home follicular test day, and were given these tests in person to remove practice effects. Subjects were instructed on the use of the ovulation kit at the same time. Test products were given to the subject along with instructions on how to follow the testing procedure and meal plan for the testing days.

TABLE 3
FOLLICULAR PHASE SCHEDULE

| Day | Activity |
|---|---|
| Every evening | Fill out written PMS symptomatology calendar |
| Day 8 | Come to study office and take all tests in person to clarify any questions and remove practice effects.<br>Learn to use an ovulation kit at this time.<br>Take monthly supply of carbohydrate preparations<br>Learn how to follow the testing procedure and meal plan for testing days. |
| Day 9 | Call-in for acute appetite, mood, and cognitive tests at 5:30 PM (these times correspond to times tests will be taken during the luteal phase). |
| Day 10 | Call-in for acute appetite and mood tests at 5:30 PM (these times correspond to times tests will be taken during the luteal phase). |

Luteal phase schedule.

The schedule outlined in Table 4 was followed by subjects during the luteal phase of their cycle. The subject's Daily Diary was monitored carefully after ovulation to verify a worsening of mood and determine the appropriate day to begin the 9:00 AM test day screening.

TABLE 4
LUTEAL PHASE SCHEDULE

| Day | Activity |
|---|---|
| Every evening | Call in PMS symptomatology calendar |
| Approximately seven days after ovulation | Called by investigator at 9:00 AM to determine severity of premenstrual symptomatology using the POMS and Misery Index measures.<br>*If Delta POMS > 30 (The difference between luteal and follicular scores of the sum of Tension, Depression, anger, and Confusion, or TDAC); and Misery Index > 5: begin Day 1 Intervention. (Since there are 26 TDAC questions with a maximum total score of 104, this represents about a 30% worsening of mood.)<br>*Otherwise: if the severity of the subject's PMS symptoms is not sufficient enough to allow testing, then she will be told that she will be called the next day.<br>*Subjects will not be tested unless they experience their typical PMS symptoms, and if they do not they will be asked to participate in testing during another menstrual cycle until they have been tested during two cycles or they will be dropped from the study. |
| Intervention Day 1 | Follow meal plan<br>3:45 PM: Call study office for Time = 0, "pre-intervention"<br>4:00 PM Drink beverage in less than 5 minutes<br>4:30 PM Call study office for mood and appetite tests<br>5:30 PM Call study office for mood, appetite, and cognition tests |

TABLE 4-continued

LUTEAL PHASE SCHEDULE

| Day | Activity | |
|---|---|---|
| | 7:00 PM | Call study office for mood and appetite tests |
| Intervention Days 2 and 3 | Follow meal plan | |
| | 9:00 AM | Drink beverage in less than 5 minutes |
| | 4:00 PM | Drink beverage in less than 5 minutes |
| Intervention Day 4 | 9:00 AM | Drink beverage in less than 5 minutes |
| | 3:45 PM | Call study office for Time = 0, "pre-intervention" measurement of mood and appetite |
| | 4:00 PM | Drink beverage in less than 5 minutes |
| | 5:30 PM | Call study office for mood, appetite, and cognition tests |
| Intervention Day 5 until menses | Same as intervention Days 2 and 3 | |

If the subject met the criteria for severity of PMS symptomatology, (i.e., the difference between luteal and follicular scores of the POMS Tension, Depression, Anger, and Confusion scores must be greater than 30 and the Misery Index must be 5 or more), then the subjects entered the first day of that month's testing regimen. (The 4 POMS TDAC scores were used to reduce the number of questions asked of the subject and therefore increase compliance. Fatigue and vigor scores were not being used in the total.) Subjects were not tested unless they experienced their typical PMS symptoms.

COMPOSITIONAL INFORMATION

The placebo was an iso-caloric mixture of 2 parts carbohydrate and 1 part protein. The volume of both the composition and placebo was similar: 7.5 ounces (about 270 mL). Composition A is a carbohydrate blend of the present invention, Example 1. Composition B is 15 g. casein protein and 32.5 g dextrose. Composition C is 47.5 g of galactose and dextrose (about 83%:17%). During the testing period a meal plan was followed. Meals were consumed at least 3 hours before composition administration and not for 3 hours after administration. Coffee, tea, and other caffeinated beverages were taken as usual. Subjects were allowed only water between meals and during the testing intervals.

The composition ingredients were all generally recognized as safe (GRAS) without limitations; the compositions themselves were therefore also GRAS; and the compositions (and the placebo) are formulated in full compliance with all good manufacturing practice regulations of the Food and Drug Administration (FDS).

Statistical Analysis

This study used a repeated measures Latin Squares design to enable statistical adjustment for anticipated order effects. The first analysis was, therefore, k, a repeated measures analysis of the primary dependent variables with planned comparisons for order effects which was negative. Whether Compositions A, B, or C was given to subjects first, second, or third had no effect on the results obtained for that Composition on any of the dependent variables.

Since intersubject variation from cycle to cycle was expected to be large in this population and since T0 score was the criterion for study participation each month, statistical adjustment was made using the T0 score as the covariate. Repeated measures ANOVAs were then conducted using the change from T30 to T90 for the individual Appetite ratings and the change from T90 to T180 for both the total of the scales on the Mood Questionnaire [TDAC], which was the criterion for participation, and, subsequently, for each scale as the dependent variables, and Composition as the repeated measure. Pairwise comparison among adjusted Composition means were tested for significance using a Least Squares procedure.

Results

MOOD:

An average decrease in TDAC from T90 to T180 (adjusted by T0) of 8.78 was seen in subjects after ingesting Composition A. Compositions B and C caused a decrease in TDAC of −1.25 and 0.44 respectively. Repeated measures analyses, by Composition of the difference of scores from T90 to T180 (from the criterion Mood Questionnaire measured, TDAC and adjusted by T0 to control for interindividual variability) showed a significant Main effect by Composition A [$p<0.04$]. Least Squares Means comparisons revealed that this was clearly due to the effect of Composition A in reducing TDAC by an average of 8.78 points, whereas Composition B produced a 1.25 point increase in TDAC and Composition C only a 0.44 decrease over this same time interval. The result obtained with Composition A was statistically significant in comparison to both Composition B [$p<0.02$] and Composition C [$p<0.04$]. There was no difference between Composition B and C. This finding demonstrates that on the criterion mood changes used to define PMS in this study [TDAC], Composition A produced a significant improvement in the subjects' self-perception of their overall mood state.

MOOD

An average decrease of Anger ratings from T90 to T180 (adjusted by T0) of 4.37 was seen in subjects after ingesting Composition A. Compositions B and C caused a decrease in TDAC of −1.30 and 0.23 respectively. Repeated measures analyses, by Composition of the difference scores from T90 to T180 for the individual mood ratings (adjusted by T0 to control for interindividual variability) showed a significant Main effect by Composition A [$p<0.02$] for the Anger scale. Least Squares Means comparisons revealed that this was due to Composition A being significantly more effective than either Composition B [$p<0.05$] or Composition C [$p<0.01$] in reducing anger ratings from T90 to T180.

Average decreases of depression ratings from T90 to T180 (adjusted by T0) for Compositions A, B, and C were 1.77, −0.9, and 0.61 respectively. Average decreases of tension ratings from T90 to T180 (adjusted by T0) for Compositions A, B, and C were 3.17, 0.13, and −0.19 respectively. For Depression and Tension, there was no Main effect by Composition but planned comparisons showed that Composition A appeared more effective than Composition B in reducing Depression ratings from T90 to T180 [$p<0.05$] and showed a trend toward being more effective than either composition B [$p<0.09$] or Composition C [$p<0.07$] in reducing Tension ratings. There were no significant findings for the subjects' Confusion ratings.

APPETITE

Repeated measures analyses, by Composition, of the difference scores from T30 to T90 for all of the Appetite variables (adjusted by T0 to control for interindividual variability) showed that there was no Main effect by Composition for subjects' estimate of either their total appetite, fat, protein, or fiber craving. For carbohydrate craving, however there was a significant Main effect by Composition A [0.78, $P<0.03$] and planned comparisons showed that Composition A was significantly more effective than either Composition B [−0.06, P<0.04] or Composition C (−0.44, P<0.01) in reducing carbohydrate cravings from T30 to T90 with late luteal baseline controlled by adjusting for T0.

DISCUSSION

Results of the POMS questionnaire were evaluated and scored. Compared with placebo, treatment with carbohydrate blends of present invention was associated with an improvement in PMS symptoms as judged by decreases in POMS scores including depression, tension, and anger.

These results confirm that, considering a subjects' monthly late luteal variability (T0 Covariate), Composition A was effective in reducing subject's overall late luteal mood rating (TDAC). As this total mood rating was the basis for determining that the subjects were actually experiencing PMS which was sufficiently elevated in comparison to their follicular rating to trigger their participation, these findings can be taken to demonstrate that the compositions of the present invention are beneficial in reducing the mood changes associated with PMS as defined in this study. When the mood scales are analyzed individually, this effect proves to be particularly robust for Anger. There was a significant effect of Composition A in decreasing subjects' late luteal estimates of their Carbohydrate craving at a time of day when appetite ratings and carbohydrate craving in particular might be expected to be increasing. Overall, the findings of this study strongly indicate that the compositions of the present invention treat, ameliorate or manage some of the mood and appetite changes associated with Pre-Menstrual Syndrome.

EXAMPLE 4

Blood samples were obtained from subjects at various times before and after consumption of carbohydrate blends of the present invention to determine the ratio of T:LNAA. Subjects administered with Composition A, a carbohydrate blends of the present invention, had a T:LNAA ratio of 0.217±0.025 after ingestion compared with a 0.168±0.016 pre-ingestion measurements and compared with carbohydrate blends containing proteins and other constituents. Further, there was an earlier onset and greater increase of T:LNAA using blends of the present invention over normal carbohydrates (bagel, juice, or potato).

The experimental results show compositions of the present invention comprising novel carbohydrate blends relieve the symptoms of PMS in human subjects.

Various modifications of the invention in addition to those shown and described herein will be apparent to those skilled in the art from the foregoing description. Such modifications are also intended to fall within the scope of the appended claims.

The foregoing disclosure includes all of the information deemed necessary to enable those skilled in the art to practice the claimed invention. Because the cited applications may provide further useful information these cited materials are hereby incorporated by reference in their entirety.

What is claimed is:

1. A composition for alleviating or managing symptoms associated with pre-menstrual syndrome comprising an effective amount of an aqueous mixture of water and a rapidly digestible carbohydrate blend comprising dextrose, dextrin, maltodextrin, or a mixture thereof and starch, pre-gelatinized starch, or a mixture thereof, said aqueous mixture being essentially free of protein, having a pH of less than 6 and having a ratio of water to carbohydrate blend of about 3–12 mL of water to 1 g of carbohydrate blend.

2. The composition of claim 1 which further comprises an acidulant that maintains said pH of less than 6.

3. The composition of claim 1 which comprises about 5 mL water to one gram carbohydrate blend.

4. The composition of claim 2 in which said acidulant is malic acid.

5. The composition of claim 1 in which said pH is between about 2 and about 5.

6. The composition of claim 1 which comprises about 45 g dextrose, 3 g starch, 280 mL water, malic acid and a pH of about 2.

7. The composition of claim 1 which comprises about 80 to 85% dextrose and about 15 to 20% starch.

8. The composition of claim 1 in which said acidulant is selected from the group consisting of adipic, citric, fumaric, lactic, succinic, tartaric, ascorbic, acetic, or malic acid.

9. The composition of claim 2 in which said acidulent is citric acid.

10. The composition of claim 1 which contains not more than 1–2 grams of fat.

11. The composition of claim 1 which comprises about 20–100 g of rapidly digestible carbohydrate blend.

12. The composition of claim 1 which comprises up to 40% starch.

13. The composition of claim 1 which comprises up to 20% starch.

14. The composition of claim 1 which comprises about 15 to 20% starch.

15. The composition of claim 1 which further comprises vitamins, tryptophan, tyrosine, ovarian hormones, detoxifying agents, or diuretics.

16. A powdered composition comprising a rapidly digestible carbohydrate blend comprising dextrose, dextrin, maltodextrin, or a mixture thereof and starch, pre-gelatinized starch, or a mixture thereof, which composition is essentially free of protein and has a pH of less than 6 on mixing with water at a ratio of about 3–12 mL of water to 1 g of carbohydrate blend.

17. The composition of claim 16 which further comprises an acidulant that maintains said pH of less than 6.

18. The composition of claim 17 in which said acidulant is selected from the group consisting of adipic, citric, fumaric, lactic, succinic, tartaric, ascorbic, acetic and malic acid.

19. The composition of claim 17 in which said acidulant is citric acid.

20. The composition of claim 16 which contains not more than 1–2 grams of fat.

21. The composition of claim 16 which contains no protein.

22. The composition of claim 16 which comprises about 20–100 g of rapidly digestible carbohydrate blend.

23. The composition of claim 16 which comprises up to 40% starch.

24. The composition of claim 16 which comprises up to 20% starch.

25. The composition of claim 16 which comprises about 15 to 20% starch.

26. The composition of claim 16 which further comprises vitamins, tryptophan, tyrosine, ovarian hormones, detoxifying agents, or diuretics.

27. A method of alleviating or managing symptoms associated with pre-menstrual syndrome comprising administering a composition comprising an effective amount of an aqueous mixture of water and a rapidly digestible carbohydrate blend comprising dextrose, dextrin, maltodextrin, or a mixture thereof and starch, pre-gelatinized starch, or a mixture thereof, said aqueous mixture being essentially free of protein, having a pH of less than 6 and having a ratio of water to carbohydrate blend of about 3–12 mL of water to 1 g of carbohydrate blend.

28. The method of claim 27 in which said composition further comprises an acidulant that maintains said pH of less than 6.

29. The method of claim 27 in which said composition comprises about 5 mL water to one gram carbohydrate blend.

30. The method of claim 28 in which said acidulant is malic acid.

31. The method of claim 27 in which said pH is between about 2 and about 5.

32. The method of claim 27 in which said composition comprises about 45 g dextrose, 3 g starch, 280 mL water, malic acid and a pH of about 2.

33. The method of claim 27 in which said composition comprises about 80 to 85% dextrose and about 15 to 20% starch.

34. The method of claim 28 in which said acidulant is selected from the group consisting of adipic, citric, fumaric, lactic, succinic, tartaric, ascorbic, acetic, or malic acid.

35. The method of claim 27 in which said acidulant is citric acid.

36. The method of claim 27 in which said composition contains not more than 1–2 grams of fat and contains no protein.

37. The method of claim 27 in which said composition comprises about 20–100 g of rapidly digestible carbohydrate blend.

38. The method of claim 27 in which said composition comprises up to 40% starch.

39. The method of claim 27 in which said composition further comprises vitamins, tryptophan, tyrosine, ovarian hormones, detoxifying agents, or diuretics.

40. The method of claim 27 in which said composition is administered beginning 1 to 14 days prior to menstruation.

41. The method of claim 40 in which said administration continues for several days after onset of menstruation.

* * * * *